United States Patent
Hayakawa et al.

[11] Patent Number: 6,023,662
[45] Date of Patent: Feb. 8, 2000

[54] MEASUREMENT DEVICE, PORTABLE ELECTRONIC INSTRUMENT, AND MEASUREMENT METHOD

[75] Inventors: Motomu Hayakawa, Suwa; Chiaki Nakamura, Chiba, both of Japan

[73] Assignees: Seiko Epson Corporation, Tokyo; Seiko Instruments, Inc., Chiba-ken, both of Japan

[21] Appl. No.: 08/849,877

[22] PCT Filed: Oct. 18, 1996

[86] PCT No.: PCT/JP96/03033

§ 371 Date: Aug. 25, 1997

§ 102(e) Date: Aug. 25, 1997

[87] PCT Pub. No.: WO97/14971

PCT Pub. Date: Apr. 24, 1997

[30] Foreign Application Priority Data

Oct. 18, 1995 [JP] Japan .................................. 7-270395

[51] Int. Cl.[7] ...................................................... A61B 5/00
[52] U.S. Cl. ........................... 702/75; 600/500; 600/587; 600/503; 600/483
[58] Field of Search ............................... 702/75; 600/500, 600/587, 503, 483

[56] References Cited

U.S. PATENT DOCUMENTS 5,697,374 12/1997 Odagiri et al. ........................ 600/500
5,766,132  6/1998 Yasukawa et al. ..................... 600/503
5,776,070  7/1998 Kitazawa et al. ...................... 600/483

FOREIGN PATENT DOCUMENTS 63-210671  9/1988  Japan .
5-256883  10/1993  Japan .

*Primary Examiner*—Patrick Assouad
*Assistant Examiner*—Hien Vo
*Attorney, Agent, or Firm*—Eric B. Janofsky

[57] ABSTRACT

In a measurement device and a measurement method for determining output values by analyzing the frequency of cyclically changing detection data, such as pulse count, the output value indicating a peak in the analysis result is corrected using side lobe values that appear on both sides of said peak, and an output value having higher precision than the output value indicating the peak value is derived, such that a value closer to the original output value of the detection data can be obtained. Because the measurement device and measurement method according to the invention can improve the precision of the output value without increasing the sampling count, highly precise output values such as pulse counts can be obtained at high speeds without extending the data fetch time.

9 Claims, 11 Drawing Sheets

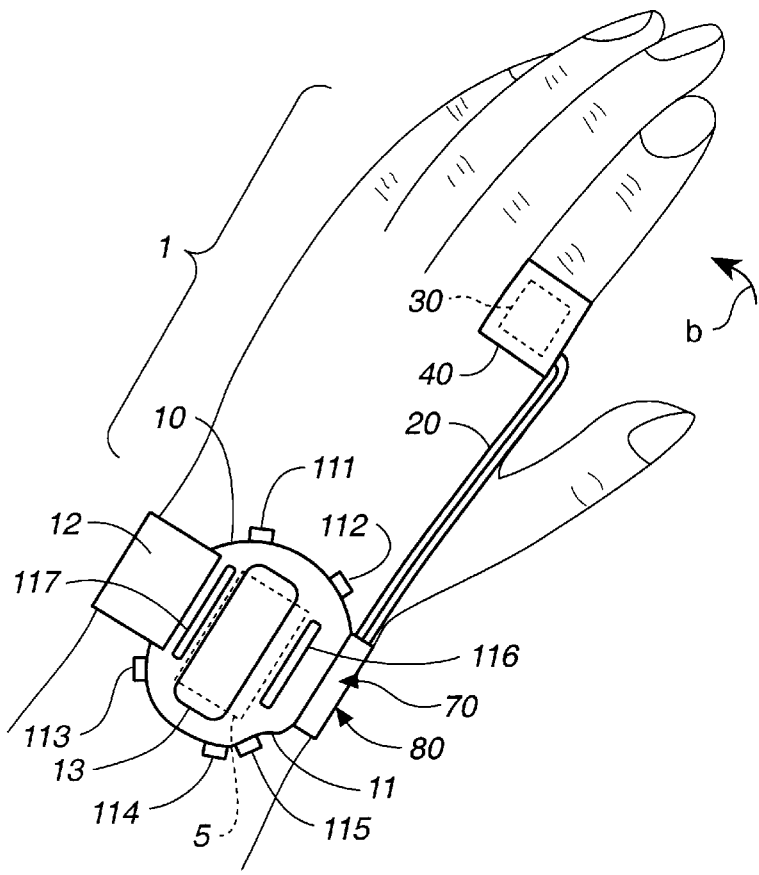
FIG._1A
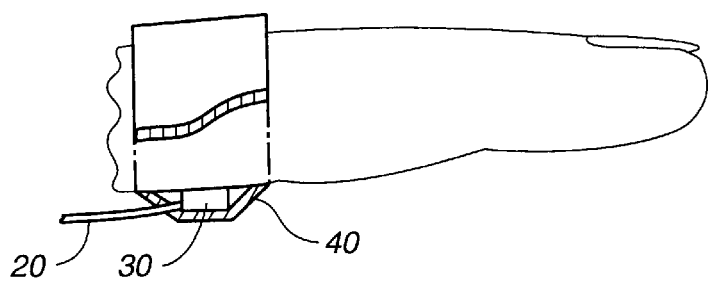
FIG._1B

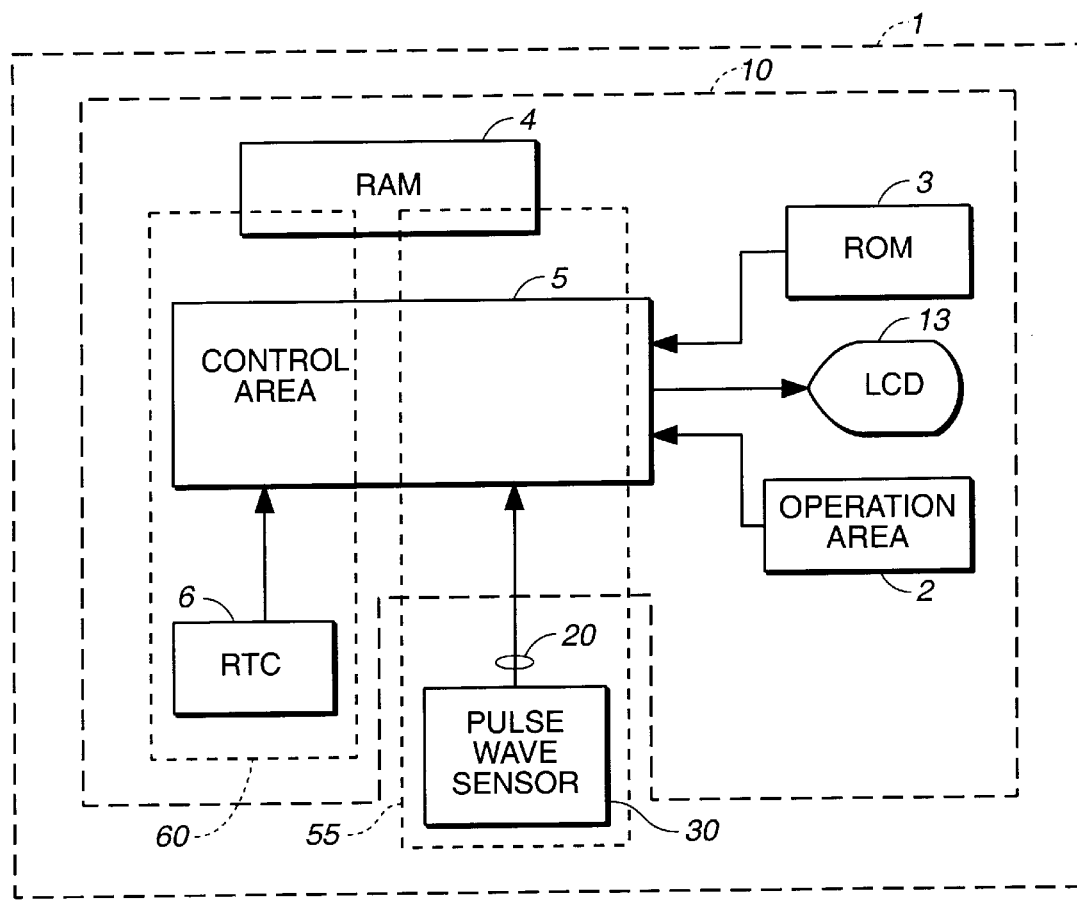
FIG._2

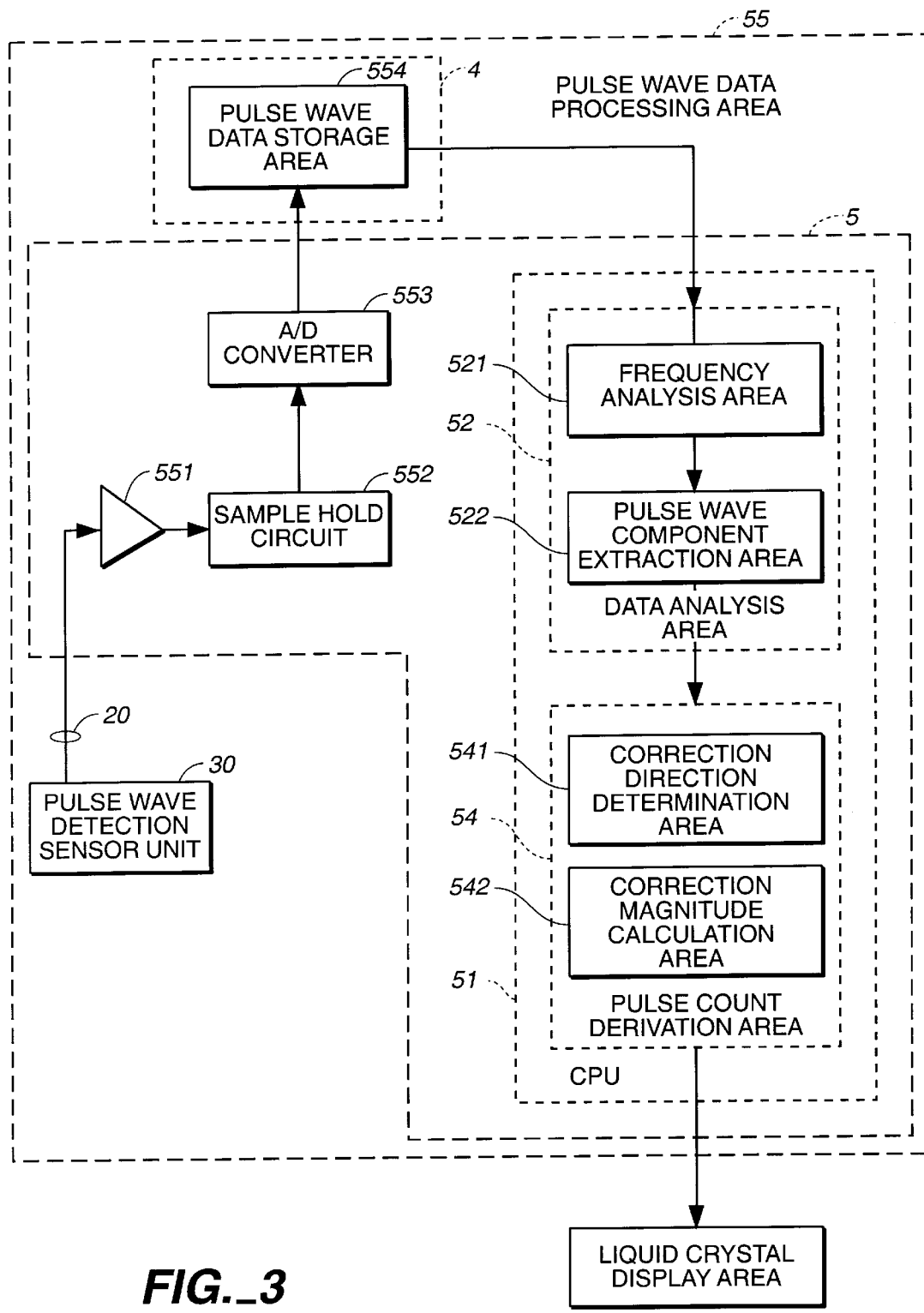
FIG._3

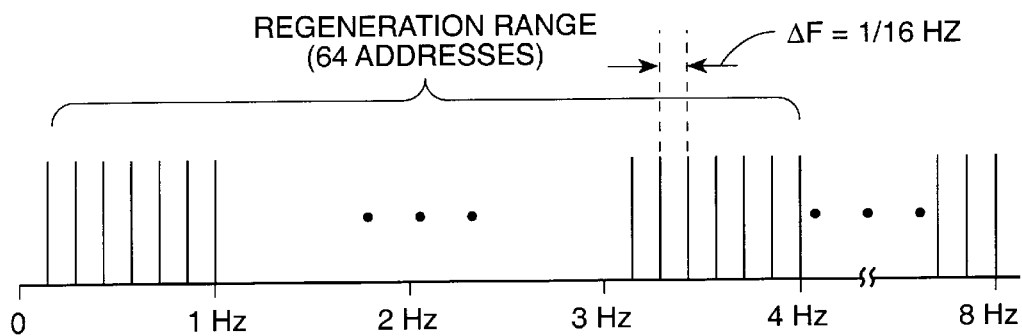
FIG._4A
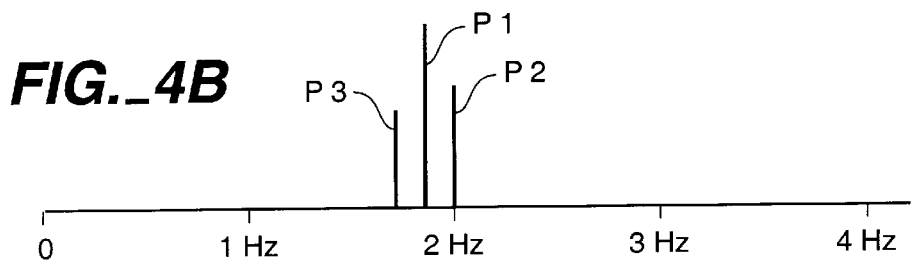
FIG._4B
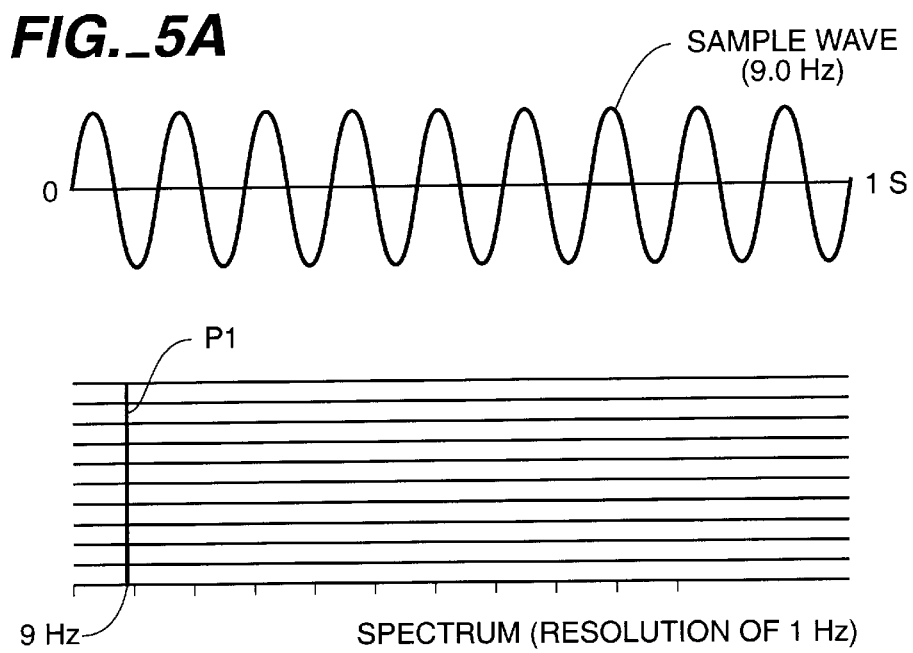
FIG._5A
FIG._5B

FIG._6A
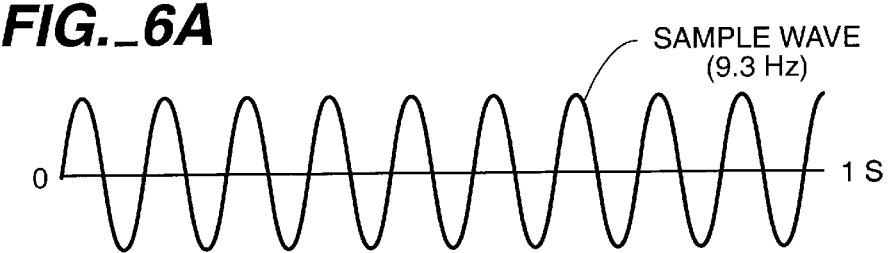
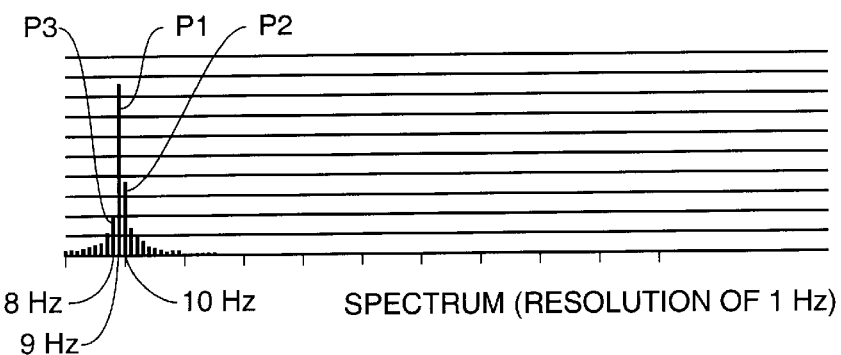
FIG._6B
FIG._7A
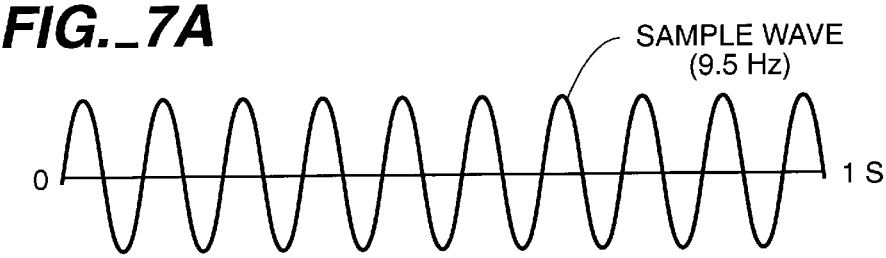
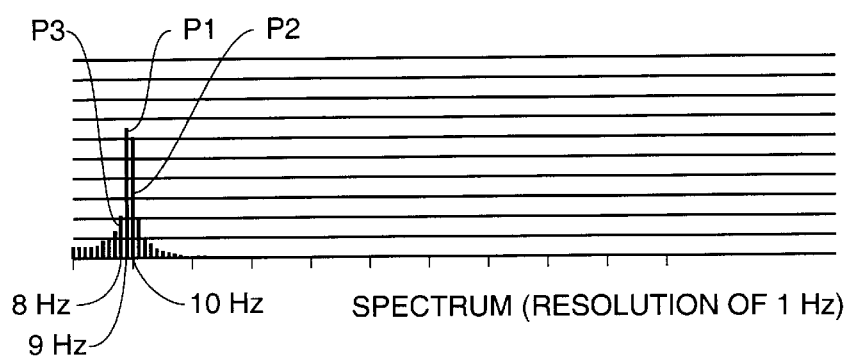
FIG._7B

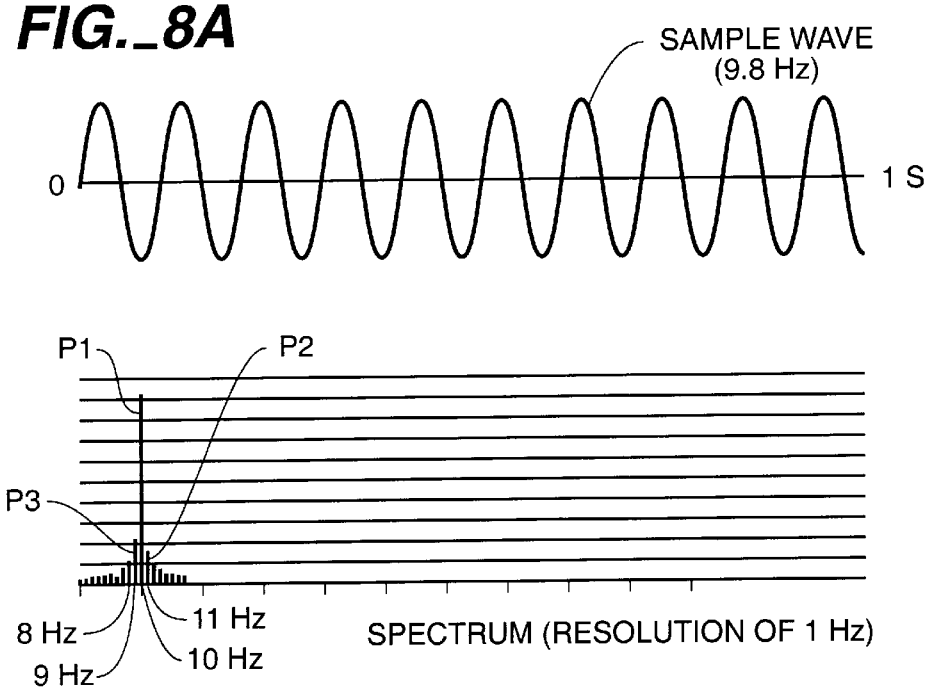
FIG._8A
FIG._8B
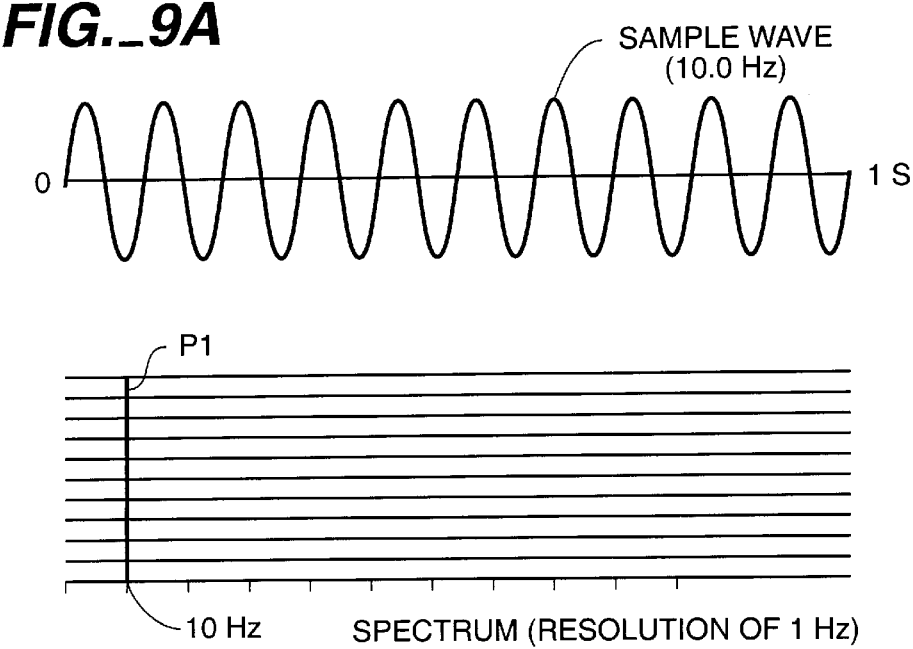
FIG._9A
FIG._9B

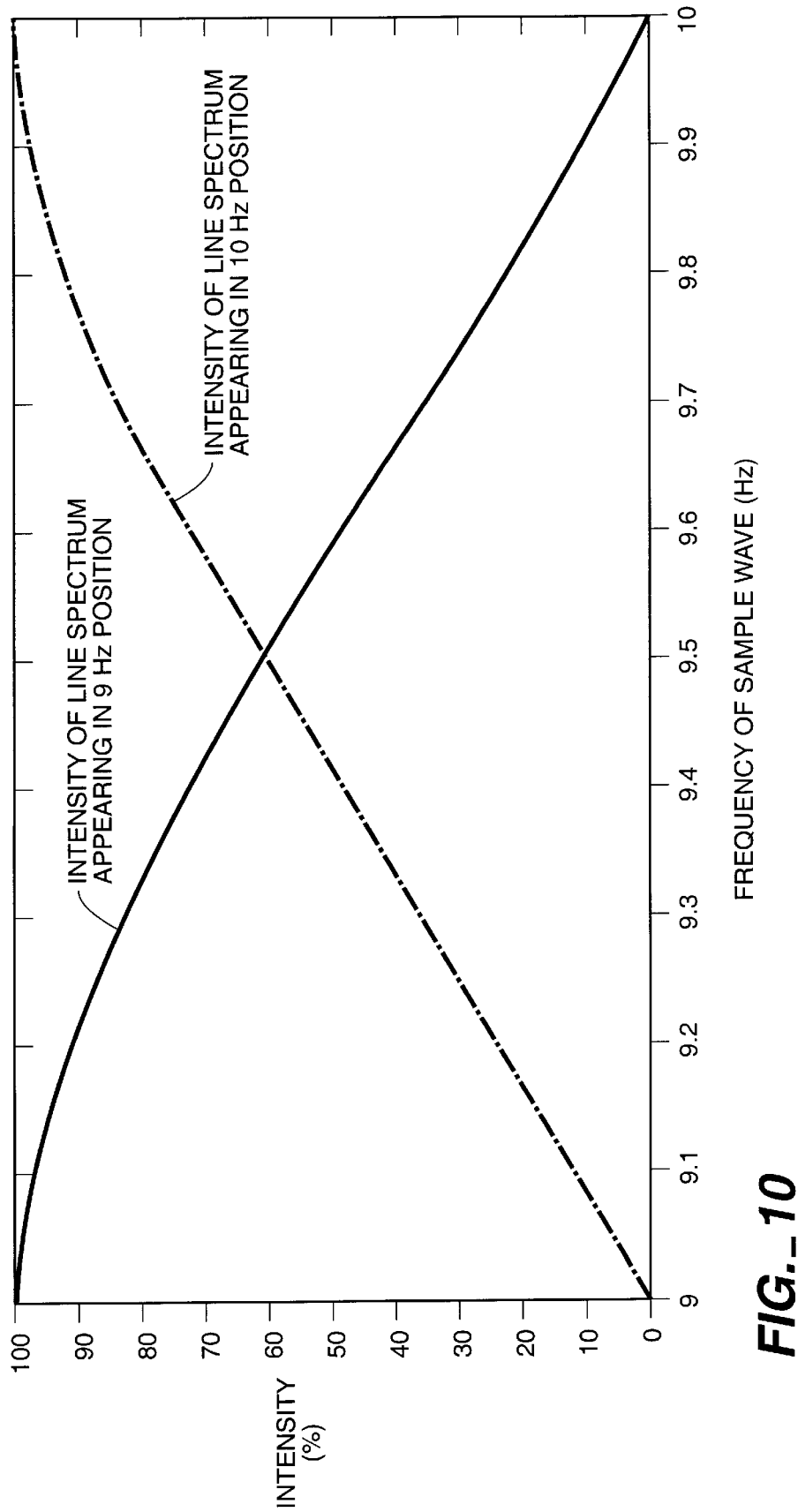
FIG._10

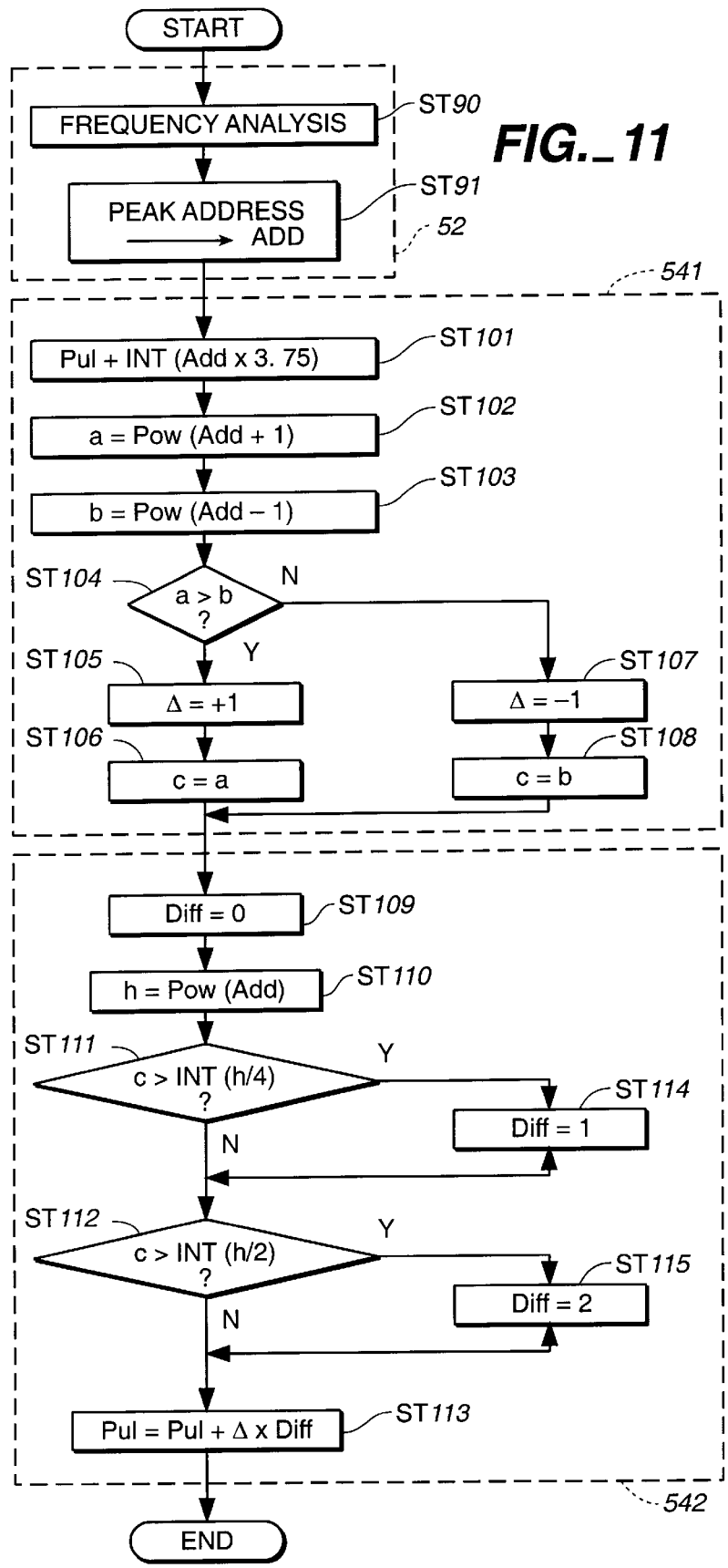
FIG._11

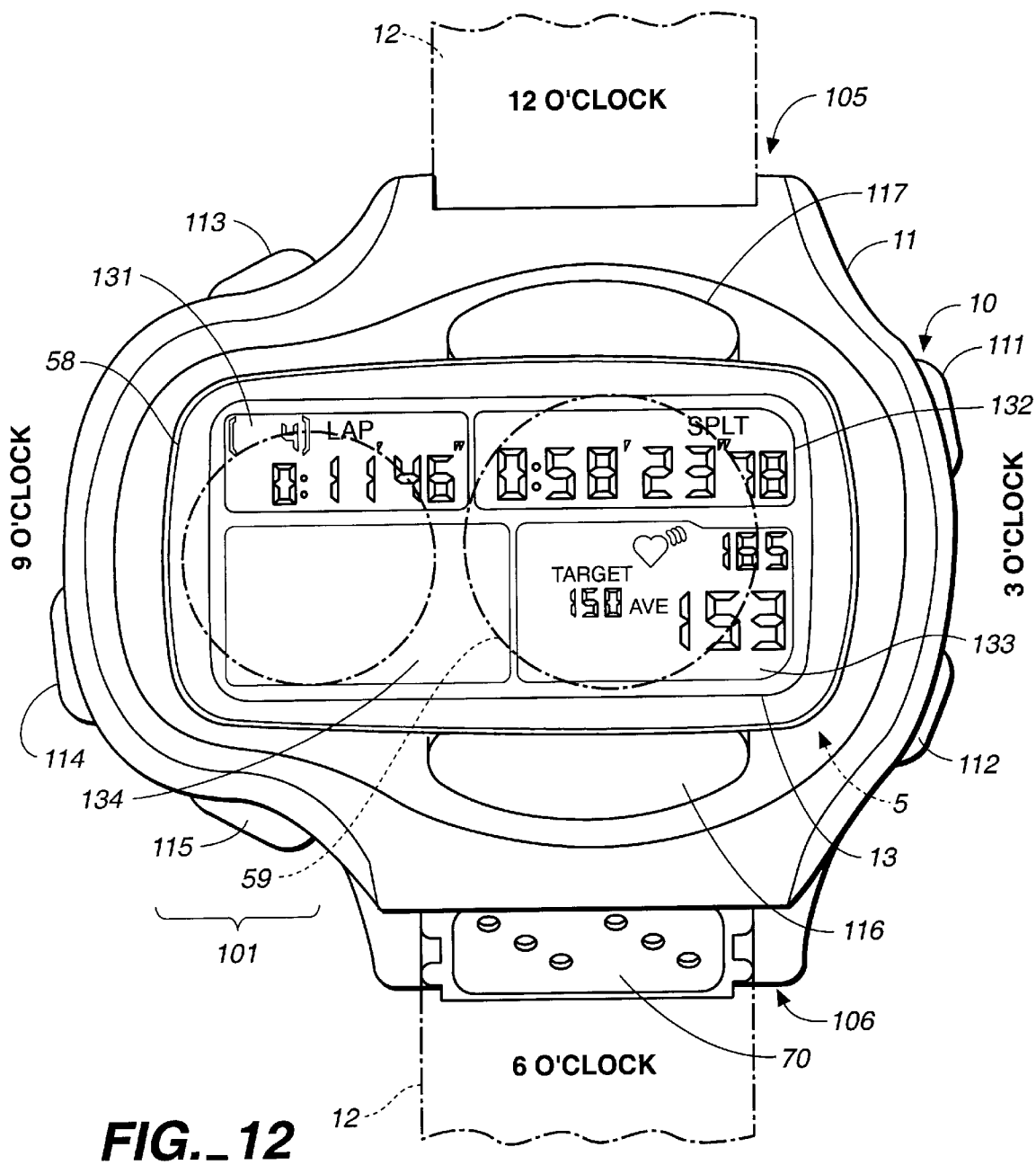
FIG._12

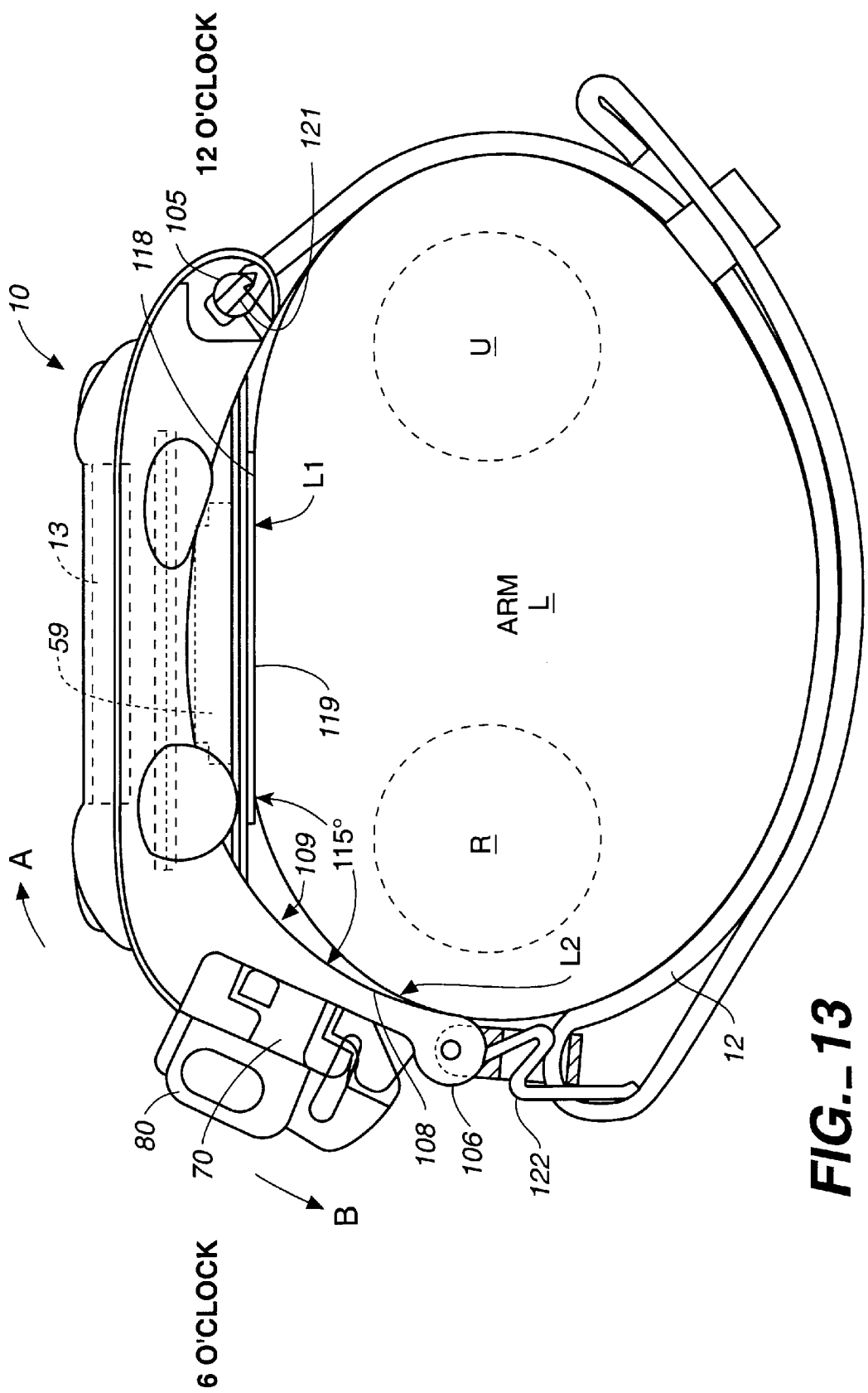
FIG._13

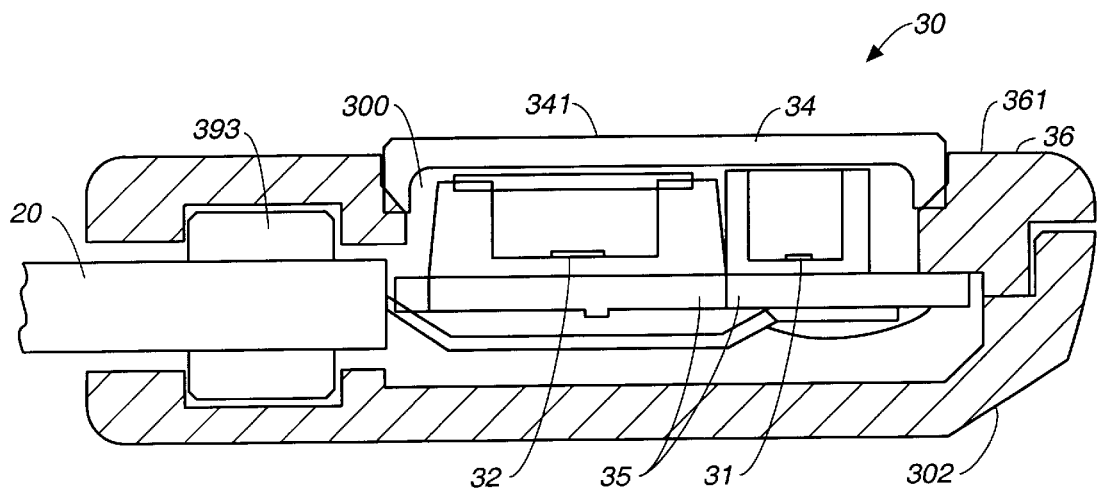
FIG._14
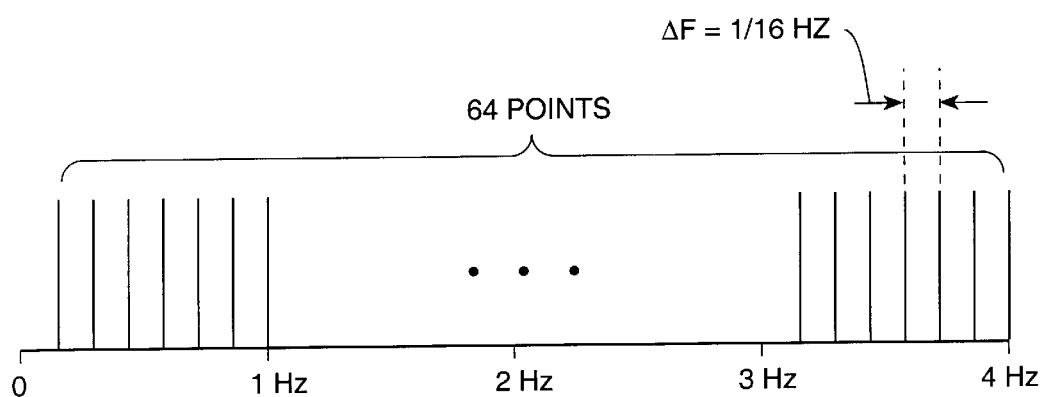
FIG._15

MEASUREMENT DEVICE, PORTABLE ELECTRONIC INSTRUMENT, AND MEASUREMENT METHOD

INDUSTRIAL FIELD OF APPLICATION

The invention relates to a measurement device and a measurement method that use a sensor to detect data that cyclically changes according to pulses or body movements, and determine cycle or frequency by analyzing the frequency of the detected value, thereby determining pulse count and body movement pitch; and more particularly, to a measurement device and a measurement method that are suitable for incorporating into or applying to small-size instruments such as portable electronic instruments.

BACKGROUND TECHNOLOGY

For using a sensor to detect data that cyclically changes according to factors such as pulse and movements of a body (body movements), e.g., pulse wave and acceleration, to determine pulse count or body movement pitch based on the detected data, a method is being considered for applying frequency analysis to the data that is detected at specified time intervals and for using the analysis result. When performing frequency analysis, it is possible to digitize the detected data and to apply a fast Fourier transformation (FFT) using a device, such as a microprocessor, capable of digital computation; and therefore analysis can be performed at a high speed using a compact device having a simple configuration. The analysis result of the digital processing can be expressed as a group of discrete line spectrums shown in FIG. 15, for example. That is, if the frequency range that can be sampled (sampling frequency) is 4 Hz and if it is possible to provide a 6-bit sampling address, 64 sampling points can be obtained. Frequency analysis can then produce a frequency having a resolution of $1/16$ Hz as the output value. For example, if a line spectrum having a peak at the 32nd address is obtained as the result of the analysis, the detected data has a frequency of 2 Hz. This translates into a pulse count measurement of 120 pulses/minute if the detected data is a pulse wave that changes according to the pulse.

However, if a line spectrum having a peak at the 33rd address is obtained as the result of the next measurement, the resulting, pulse count is 123.75 pulses/minute which would be 123 pulses/minute after digitization (integer conversion). In other words, the aforementioned system cannot output pulse counts between 120 and 123 pulses/minute. In this way, calculating a pulse count directly from the frequency of the line spectrum obtained through frequency analysis results in unnatural values and low precision. The aforementioned example can only provide a value based on the conversion of $1/16$ Hz, which is the line spectrum interval (resolution), into a pulse count, i.e., 3.75 pulses/minute, or a value that has been turned into an integer.

In order to improve the precision of the pulse count to be output, it is necessary to improve the resolution to be obtained from frequency analysis. For example, the resolution can be improved by increasing the number of sampling points, thus extending the data fetch time which is expressed as a product of sampling frequency and sampling point count. However, such a change tends to lengthen the sampling time needed for accumulating sufficient data for allowing frequency analysis because pulse count and body movement pitch have low frequencies. Even when measuring pulse with the aforementioned condition, a long data fetch time of around 16 seconds/cycle is required. Consequently, if the number of sampling points is increased to further extend the data fetch time, the time required for updating pulse count becomes extremely long, and as a result the pulse count that is displayed is for a fairly old measurement. Therefore, a portable pulse counter to be worn on the arm for realtime display of pulse measurement or a portable electronic instrument equipped with a pulse-measurement function will not be able to display pulse changes on a realtime basis, making the unit inconvenient and posing a difficulty in comprehending the wearer's condition.

Furthermore, increasing the number of sampling points results in a larger volume of data to be sampled, increasing the time required for frequency analysis. Additionally, since the address for sampling must also be increased, these factors cause both the size and cost of the device to increase. Moreover, if the address must be increased simply for increasing the number of sampling points, it will be necessary to use a processor that may be too fast for other mechanisms that are incorporated, such as a clock mechanism, which can be a problem.

If a personal computer (PC) is used for analysis, increasing the number of sampling points also increases the amount of data to be sent to and processed by the PC, causing processing speed degradation.

Therefore, the objective of this invention is to provide a measurement device and a measurement method that can provide output values, such as pulse count and body movement pitch, at high precision without increasing the number of sampling points, and thus can output more natural values.

Another objective of the invention is to provide a measurement device and a measurement method that can process data within a short time period without extending the data fetch time or processing time by making it possible to display highly precise output values without increasing the number of sampling points, and that can output pulse count and body movement pitch on a realtime basis in a portable device or at a high speed in a processing device such as a personal computer.

Still another objective is to provide a compact and inexpensive portable electronic instrument, in which multiple functions are incorporated in addition to pulse-count and pitch measurement functions, that can produce highly precise values using a simple configuration based on the present invention.

DISCLOSURE OF THE INVENTION

In the present invention, in order to obtain highly precise output values without increasing the number of sampling points, the output value indicating a peak is corrected using the side lobe values that appear on both sides of the peak value during frequency analysis. That is, the measurement device according to the invention has an analysis means that analyzes the frequency of cyclically changing detection data obtained from a sensor and produces the analysis result as digital data of a specified resolution, and a derivation means that derives a cycle or frequency as an output value from the analysis result, such that said derivation means can correct the output value indicating a peak in the analysis result, using a side lobe value that appears adjacent to and on at least one side of the peak, and can derive an output value of the detection data at a precision that is higher than the resolution.

During frequency analysis of the detection data, if the digital value determined by the resolution of the analysis means, i.e., a certain sampling point (address), matches the frequency of the detection data, an extremely sharp peak is obtained for that address. In contrast, if the frequency of the detection data does not match the address, i.e., the frequency is located between two addresses, subpeaks indicating side lobes will appear on both sides of and adjacent to the peak. Therefore, it is possible to correct the output value determined from the peak address (output value indicating the address) using the output values determined from the side lobe addresses (output values indicating the side lobes), and thus the output value of the data that is located between the output value indicating the peak and the output value indicating a side lobe can be determined at a higher precision.

As explained above, because the measurement device according to the invention can provide the output value of the detection data at a precision higher than the resolution without increasing the number of sampling points, it can process data and output more natural values within a short time period without extending the data fetch time or processing time. Therefore, in a portable electronic instrument that has both a control device that can process signals from a sensor and a display device that can display the output from this control device, wherein sad control device is equipped with the aforementioned analysis function and a determination function, and into which other functions in addition to the function for measuring cyclical detection data can be incorporated, it is possible to output pulse count and body movement pitch values on a realtime basis and moreover to use a compact and inexpensive configuration.

As for a correction method using side lobes, one possible method is to perform correction while comparing the peak and side lobe intensities after converting them into patterns. Here, by providing the determination means with a correction direction determination means that identifies the side lobe to be used for correction by comparing the intensities of the side lobes on both sides of the peak, and with a correction magnitude calculation means that determines the correction magnitude by comparing the intensity of the peak with that of the side lobe identified to be used for correction and then corrects the output value indicating the peak, both the magnitude and direction of the correction can be obtained in a simple process.

The correction magnitude calculation means uses a digital value close to the mesial magnitude of the resolution as the maximum correction magnitude and then calculates a correction magnitude using a specified function to convert the ratio of the intensity of the side lobe identified to be used for correcting the peak intensity into a digital value, and thus can determine an appropriate correction magnitude within a short time period.

Such a method that uses a side lobe to correct the output value indicating the peak in order to determine the output value of the detection data at a high precision, can be applied to cases in which detection data is analyzed in a processing device such as a personal computer. That is, the present invention can provide a measurement method having the steps described below.

1. Analysis process that analyzes the frequency of the cyclically changing detection data obtained from a sensor and that produces the analysis result as digital data of a specified resolution 2. Derivation process that, when deriving a cycle or frequency as an output value from the analysis result, corrects the output value indicating a peak in the analysis result, using a side lobe value that appears adjacent to and on at least one side of the peak, and derives an output value of the detection data at a precision that is higher than the resolution.

As in the aforementioned measurement device, by providing the derivation process with a correction direction determination process that identifies the side lobe to be used for correction by comparing the intensities of the side lobes on both sides of the peak, and with a correction magnitude calculation process that determines the correction magnitude by comparing the intensity of the peak with that of the side lobe identified to be used for correction and then corrects the output value indicating the peak, the correction process can be performed within a short time period. Additionally, the correction magnitude calculation process uses a digital value close to the mesial magnitude of the resolution as the maximum correction magnitude and then calculates a correction magnitude using a specified function to convert the ratio of the intensity of the side lobe identified to be used for correction relative to the peak intensity into a digital value, and thus can calculate a more accurate correction magnitude within a short time period.

Such a measurement method according to the present invention can be provided as a software program equipped with the aforementioned processes, and can be provided as a program stored in a medium such as a magnetic recording medium or ROM that can be read by a computer or microprocessor.

BRIEF EXPLANATION OF THE DRAWINGS

FIGS. 1A and 1B are diagrams showing the external appearance of a portable electronic instrument in which a pulse count measurement function using the measurement method according to the invention has been installed, and how this instrument is used.

FIG. 2 is a block diagram showing a schematic configuration of the portable electronic instrument shown in FIGS. 1A and 1B.

FIG. 3 is a block diagram showing a schematic configuration of the pulse data processing area of the electronic instrument shown in FIGS. 1A and 1B.

FIGS. 4A and 4B are diagrams schematically showing the spectrum obtained from analyzing the frequency of a pulse signal in the pulse data processing area shown in FIG. 3.

FIGS. 5A and 5B are diagrams showing the waveform of a sample wave and the result of its frequency analysis to explain the correction principle of the invention; FIG. 5A is a waveform diagram showing a sample wave of 9.0 Hz; and FIG. 5B is the analysis result (spectrum) obtained from analyzing the frequency of the detection data in which the sample wave was detected.

FIGS. 6A and 6B have the same purpose as FIGS. 5A and 5B; FIG. 6A is a waveform diagram showing a sample wave of 9.3 Hz; and FIG. 6B is the analysis result (spectrum).

FIGS. 7A and 7B have the same purpose as FIGS. 5A and 5B; FIG. 7A is a waveform diagram showing a sample wave of 9.5 Hz; and FIG. 7B is the analysis result (spectrum).

FIGS. 8A and 8B have the same purpose as FIGS. 5A and 5B; FIG. 8A is a waveform diagram showing a sample wave of 9.8 Hz; and FIG. 8B is the analysis result (spectrum).

FIG. 9A and 9B has the same purpose as FIGS. 5A and 5B; FIG. 9A is a waveform diagram showing a sample wave of 10.0 Hz; and FIG. 9B is the analysis result (spectrum).

FIG. 10 is a graph that summarizes FIGS. 5A, 5B, 6A, 6B, 7A, 7B, 8A, 8B, 9A and 9B shows the changes in the intensities of the line spectrums that appear in the positions of 9 Hz and 10 Hz when the frequency of the sample wave is changed from 9.0 Hz to 10 Hz.

FIG. 11 is a flow diagram showing the processing in the pulse wave data processing area of the present example.

FIG. 12 is the top-view diagram of the device main body of the portable electronic instrument shown in FIG. 1.

FIG. 13 is a diagram of the device main body of the portable electronic instrument shown in FIG. 1, viewed from the 3 o'clock direction of the watch.

FIG. 14 is a cross-section diagram of the pulse-detection sensor unit used in the portable electronic instrument shown in FIG. 1.

FIG. 15 is a diagram showing an example of the result of frequency analysis of cyclically changing detection data.

BEST EMBODIMENT FOR IMPLEMENTING THE INVENTION

Next, an embodiment of the invention will be explained with references to the drawings.

FIGS. 1A and 1B show a wrist-watch type portable electronic instrument equipped with the measurement function according to the invention. This portable electronic instrument 1 has a pulse count measurement function that can measure and display a pulse wave, in addition to a clock function that can be used as a wrist watch, and is designed such that the measurement method according to the invention can be applied when deriving a pulse count from a pulse wave. As shown in the figure, portable electronic instrument 1 in this embodiment is equipped with device main body 10 possessing a wristwatch structure, and this main body contains control area 5, etc. for implementing the aforementioned various functions. Liquid crystal display device 13, which displays various data such as time and pulse count as well as performing a user-interface function, is installed on the surface of main body 10; and furthermore, multiple operation switches 111, 112, 113, 114, 115, 116, and 117 for controlling the various functions are installed on the top and side surfaces of main body 10. Additionally, pulse wave detection sensor unit 30 is connected to main body 10 via cable 20, so that pulse waves from the finger can be detected. Wristband 12, which is wrapped around the wrist from the 12 o'clock direction of the wristwatch (hereafter, all directions relative to main body 10 will be indicated in terms of clock directions) and fastened in the 6 o'clock direction, is installed in said main body 10, enabling device main body 10 to be detachably mounted on the user's wrist.

FIG. 2 shows a schematic configuration of electronic instrument 1 of this embodiment in a block diagram. Electronic instrument 1 of this embodiment is configured around control area 5 which comprises an element such as a microprocessor, and is provided with ROM3 which stores the programs and data necessary for processing in said control area 5, RAM4 to be used as a temporary storage area for processing and for accumulating measurement data, etc., and control area 2 for controlling control area 5. Control area 2 is provided with various switches 111 through 117 installed on the top or side surfaces of main body 10 as explained above. Additionally, electronic instrument 1 of this embodiment is equipped with liquid crystal panel 13 for user interface as explained above, and said liquid crystal display device 13 displays information such as time, measured data, and processing mode.

Electronic instrument 1 of this embodiment is additionally provided with realtime clock (RTC) unit 6 which has an oscillation function for timing, a function for measuring time of day and date, etc.; and clock processing area 60 which performs clock operations as a clock or stopwatch is configured utilizing the functions of this RTC unit 6. Additionally, electronic instrument 1 of this embodiment is equipped with pulse wave processing arena 55 which can measure pulses by using control area 5 to process the signals from pulse wave sensor 30 which is connected to main body 10 via cable 20.

The Pulse Wave Data Processing Area

FIG. 3 shows more details of pulse wave data processing area 55 of this embodiment. Pulse wave data processing area 55 of this embodiment is designed to be able to determine a pulse count based on the result that is input from pulse wave detection sensor unit 30, and to display the determined value on liquid crystal display device 13.

As will be described in detail below, pulse wave data processing area 55 of this embodiment is equipped with pulse wave detection sensor unit 30 which is mounted on a finger and can detect pulse waves as analog signals, and can provide analog signals to operation amplifier 551 of control area 5 housed inside main body 10 from said pulse wave detection sensor unit 30 via cable 20. The detection data of the analog signals detected by pulse wave detection sensor unit 30 is amplified by operation amplifier 551 and is sampled for each frequency by sampling hold circuit 552 of control area 5. The sampled result is converted into a digital signal by A/D converter 553 of control area 5 and is temporarily accumulated in pulse wave data storage area 554 of RAM4. The frequency of the data accumulated in said pulse wave data storage area 554 is analyzed to determine a pulse. Of course, it is also possible to use a processing device to analyze the data accumulated in pulse wave data storage area 554 by transferring the data to a processing device such as a personal computer or by supplying the data via a storage medium.

Furthermore, in pulse wave data processing area 55 of this embodiment, CPU51 of its control area 5 is provided with data analysis area 52 which can obtain analysis results by applying as frequency analysis, fast Fourier transformation (FFT) to the data stored in pulse wave data storage area 554, and with pulse count derivation area 54 which derives a pulse count from the analysis result. Data analysis area 52 is provided with frequency analysis area 521 which performs FFT processing, and with pulse wave component extraction area 522 which extracts the address and intensity of the peak and the address and intensity of the side lobe, described below, from the frequency analysis result and supplies this information to pulse count derivation area 54. Then, pulse count derivation area 54 calculates the frequency of the detection data obtained from pulse wave detection sensor unit 30, and a pulse count can be obtained from that frequency.

Pulse wave data processing area 55 of this embodiment uses general-purpose sample hold circuit 552 having a sampling frequency of 8 Hz and which can use 7 bits (128 points) as the sampling address. Of the data sampled by this sample hold circuit 552, 4 Hz which is equivalent to a pulse count of between 0 and 240 pulses/minute and 64 addresses (64 sampling points) are used for analyzing frequencies and evaluating the analysis results. Therefore, the digital data obtained as the result of frequency analysis by cycle analysis area 521 becomes discrete data having a resolution of 1/16 Hz. When this data is expressed as line spectrums, the result is 64 line spectrums that discretely appear at 1/16 Hz intervals as shown in FIG. 4A. Therefore, if the address indicating the maximum value (peak) of the analysis result is simply converted into a pulse count, a value of 3.75 pulses/minute which results from converting the resolution of 1/16 Hz into a pulse count is obtained. However, this level of precision is insufficient as explained above, resulting in unnatural display when pulse count, must be displayed on a realtime basis.

For this reason, in pulse wave data processing area 55 of this embodiment, pulse count derivation area 54 which derives pulse counts is provided with correction direction determination area 541 which focuses on side lobes P2 and P3 which appear adjacent to and on both sides of peak P2 and determines the direction (+ or − direction) in which to correct the frequency indicating peak P1 based on said side lobes P2 and P3, and with correction magnitude calculation area 542 which determines a correction magnitude by comparing the intensities of side lobes P2 and P3 with the intensity of peak P1, as shown in FIG. 4B.

Although details will be provided below, correction direction determination area 541 of this embodiment identifies the side lobe to be used for correction by comparing the intensities of side lobes P2 and P3; and the direction of the identified side lobe, e.g., side lobe P2 in FIG. 4B, i.e., the + direction, is determined to be the correction direction. Correction magnitude calculation area 542 then calculates a correction magnitude by comparing the intensity of the identified side lobe P2 with that of peak P1. If the frequency of the detection data (hereafter referred to as "original frequency") is close to side lobe P2, the position of side lobe P2 will become that of peak P1. By taking this fact into account, the maximum value of the correction magnitude is set to a digital value close to the mesial magnitude of the resolution. Pulse count derivation area 54 in this embodiment is designed to output a pulse count as an integer, and the maximum correction value is set to 2 since the resolution is 3.75 pulses/minute as explained above. The intensity of the identified side lobe P2 is compared with that of peak P1 and the resulting ratio is designated as Rp. The correction value is determined using a function that produces correction value Diff of 0 if Rp is ¼ or smaller, correction value Diff of 1 if Rp is between ¼ and ½, and correction value Diff of 2 (the maximum value) if Rp is ½ or greater. In this embodiment, this function is implemented using an algorithm.

Overview of Correction

Before explaining the specific processing performed by pulse count derivation area 54, an overview of the correction that can be performed using the side lobes that appear adjacent to and on both sides of the peak spectrums will be explained. Note that in the example below, data is sampled using a sampling method having a 1-Hz resolution to obtain frequency analysis result, in order to make the correction overview easier to explain. Furthermore, a wave whose frequency changes from 9 Hz to 10 hz is used as a sample wave. This sample wave is sampled for the specified number of sampling count and is converted into digital data. FFT processing is then applied to this digital data to produce the analysis result. The analysis result is shown using line spectrums which appear discretely at 1-Hz intervals.

In FIGS. 5A and 5B, the result of frequency analysis of the sample wave having a frequency of 9.0 Hz. As these figures show, when the frequency of the detection data in which the 9.0 Hz sample wave was detected is analyzed, line spectrum P1 showing a sharp peak appears in the 9 Hz position.

In contrast, as shown in FIGS. 6A and 6B, when the frequency of the detection data in which 9.3 Hz sample wave was detected is analyzed, line spectrum P1 showing a peak appears in the 9 Hz position, and additionally line spectrums P2 and P3 indicating side lobes having smaller magnitudes than line spectrum P1 appear in the positions of 10 Hz and 8 Hz on both sides of the first peak. The intensity of line spectrum P2 appearing in the 10 Hz position is stronger than the intensity of line spectrum P3 appearing in the 8 Hz position, demonstrating that line spectrum P2 indicating a more intense side lobe is obtained on the + side of peak P1.

Furthermore, as shown in FIGS. 7A and 7B, when the frequency of the detection data in which 9.5 Hz sample wave was detected is analyzed, line spectrum P1 showing a peak appears in the 9 Hz position, and additionally line spectrums P2 and P3 indicating side lobes appear on both sides of the first peak. In this example, the intensity of line spectrum P2 for the 10-Hz side lobe is much stronger than the intensity of line spectrum P3 for the 8-Hz side lobe, is much stronger than line spectrum P2 for the 10 Hz side lobe shown in FIG. 6B, and is nearly equal to the intensity of peak line spectrum P1 in the 9-Hz position.

As shown in FIGS. 8A and 8B, when the frequency of the detection data in which 9.8 Hz (which is much closer to 10 Hz) sample wave was detected is analyzed, line spectrum P1 showing a peak moves to the 10 Hz position, and line spectrums P2 and P3 indicating side lobes move to the positions of 11 Hz and 9 Hz on both sides of the first peak. The comparison of the intensities of these line spectrums P2 and P3 indicating side lobes shows that the 9-Hz line spectrum P3 on the (−) side is larger.

Moreover, as shown in FIG. 9B, when the frequency of the detection data in which 10.0-Hz sample wave was detected is analyzed, line spectrum P1 showing a sharp peak appears in the 10-Hz position, and hardly any line spectrums indicating side lobes appear.

These results are summarized in FIG. 10 which shows the data, in which a sample wave whose frequency changes from 9 Hz to 10 Hz is detected, in terms of frequency analysis output. This figure shows that as the frequency of the sample wave increases, the intensity of the line spectrum appearing in the 9-Hz position gradually decreases as indicated by the solid line in FIG. 10. In contrast, the intensity of the line spectrum appearing in the 10-Hz position gradually decreases as indicated by the dot-dashed line. Based on these results, if an analysis result shown in FIG. 6B, for example, is obtained, it can be assumed that the original frequency is located between the 9-Hz frequency of line spectrum P1 indicating the peak and the position of 10-Hz frequency indicating side lobe P2 which is stronger than the other side lobe P3, and thus an original frequency of 9.3 Hz can be derived.

That is, when the intensities of two line spectrums, P1 and P2 are compared by treating line spectrum P1 indicating the peak as the target spectrum and line spectrums P2 and P3 of the side lobes that appear or both sides of P1 as the adjacent spectrums, the intensity of line spectrum P2 is stronger than that of line spectrum P3. Therefore, correcting the 9-Hz frequency of the target spectrum (line spectrum P1) to the higher frequency side (+ direction or the direction of 10 Hz) can bring the frequency closer to the original frequency. Since the difference (ratio) between the target spectrum (line spectrum P1) and line spectrum P2 indicating a side lobe with strong intensity is in the range between 1:0.4 and 1:0.6, it can be assumed that the magnitude of correction should be around 0.3 Hz.

The process in which pulse wave data processing area 55 of this embodiment analyzes the frequency of the detection data and derives a pulse count will be explained based on the flow diagram shown in FIG. 11. First, frequency analysis (FFT) process is performed using data analysis area 52 in step ST90. The address indicating the peak is obtained from the result of the analysis in step ST91 and is set in variable Add which indicates the identified address.

Next, correction direction determination area 541 is used to determine the correction direction. First, in step ST101, address Add indicating the peak is multiplied by 3.75 pulses/minute which is the resolution of the pulse wave data processing area 55 of this embodiment, to obtain pulse count Pul which is the output value indicating the peak. This pulse count Pul is the value before correction.

Next, in steps ST102 and ST103, addresses Add ±1 which come before and after address Add and which indicate side lobe addresses are specified, and the intensities of the side lobes are set in variables a and b. In step ST104, variables a and b are compared. If variable a is larger than variable b, i.e., if the intensity of the side lobe in the + direction is stronger than the intensity of the side lobe in the − direction, +1 is set in variable Δ which indicates a correction direction in step ST105, and additionally the intensity (variable a) of the side lobe in the + direction (on the higher frequency side) is set in variable c in step ST106.

On the other hand, if step ST104 determines that variable b is larger than variable a, i.e., the intensity of the side lobe in the − direction is stronger than the intensity of the side lobe in the + direction, −1 is set in variable Δ in step ST107, and additionally the intensity (variable b) of the side lobe on the −direction (on the lower frequency side) is set in variable c in step ST108. The above process identifies the side lobe to be used for correction and sets the correction direction.

Next, correction magnitude calculation area 542 is used to determine the correction magnitude and correct pulse count Pul. For this purpose, correction magnitude Diff is first cleared to 0 in step ST109. Next, in step ST110, the peak intensity is set in variable h using address Add, and in steps ST111 and ST112, whether the intensity (variable c) of the identified side lobe is ¼ or less of the peak intensity (variable h), ¼~½, or ½ or more is determined. In step ST111, the value of variable c is compared with a value that is ¼ of variable h; and if variable c is larger, 1 is set in variable Diff in step ST114. Furthermore, in step ST112, the value of variable c is compared with a value that is ½ of variable h; and if variable c is larger, 2 is set in variable Diff in step ST115. Therefore, if variable c is less than ¼ of variable h, variable Diff is set to 0; if variable c is equal to or larger than ¼ of variable h but is less than ½ of variable $h$, variable Diff is set to 1; and if variable c is equal to or larger than ½ of variable h, variable Diff is set to 2. Using the variable Diff and Δ set in the above steps, pulse count Pul corresponding to the peak address is corrected in step ST113; and if side lobe are present, pulse count Pul that is shifted toward the side lobe with a larger intensity can be obtained.

As explained above, pulse wave data processing area 55 of this embodiment is designed to compare the peak intensity and the side lobe intensities whose frequencies have been analyzed, and to use the comparison result to correct the frequency indicating the peak, in order to derive a frequency that is closer to the original frequency. In this embodiment, no correction is performed if the intensity of the side lobe to be used for correction is ¼ or less of the peak intensity, and correction of ±1 is performed depending on the direction of the side lobe to be used for correction if the side lobe intensity is in the range of ¼ to ½ of the peak intensity. Correction of ±2 is performed if the side lobe intensity exceeds ½ of the peak intensity. Therefore, even though the resolution of the pulse count obtained as the result of the frequency analysis is as coarse as 3.75 pulses/minute, the correction can produce an extremely precise pulse count with a resolution of 1 pulse/minute and a precision of ±0.5 pulses/minute.

Of course, the function (algorithm) for obtaining correction magnitude is not limited to that described above, and it is possible to calculate the correction magnitude by substituting the ratio between the peak intensity and side lobe intensity into a certain equation, instead of using an algorithm for evaluation. Of course, it is also possible to use values other than ½ or ¼, such as ⅓ and ⅔ for the intensity evaluation value. Although a tool such as a patterned table can also be used for evaluating the peak intensity and side lobe intensities, the use of the aforementioned processing method can produce sufficiently precise output values within a short time period. Furthermore, because the present invention can produce sufficiently precise output values, natural and reasonable values can be displayed even when output values must be displayed continuously.

Furthermore, because pulse wave data processing area 55 of this embodiment can improve the precision of pulse counts which are output values, without increasing the number of sampling points, highly precise pulse counts can be displayed without extending the data fetch time. Moreover, since the sampling count does not increase, the time required for FFT processing does not increase, and thus highly precise pulse counts can be calculated at high speeds. Therefore, by detecting pulse waves by mounting wristwatch-type electronic instrument 1 of this embodiment on the user's wrist, pulse counts can be displayed on electronic instrument 1 on a realtime basis, and it becomes possible to closely monitor pulse counts while the wearer is engaged in a marathon, walking, or training, and thus to understand one's own physical condition and adjust the exercise accordingly.

Additionally, because the measurement device and measurement method according to the invention do not increase sampling counts, highly precise measurements can be made using a general-purpose type or a small and compact type with a limited number of addresses for the processing mechanism such as the sample hold circuit that processes pulse waves. Therefore, the invention enables even a small and inexpensive measurement device to provide precise measurement results.

Pulse wave data processing area 55 equipped with the functions described above can be implemented as one of the functions of multi-function electronic instrument 1 as in this embodiment, or can be provided as a pulse wave counter equipped with a single function for measuring pulse waves. The pulse count determination process explained based on FIG. 11 can of course be implemented as a software program when analyzing pulse wave data using a personal computer, etc. A software program utilizing the measurement method according to the invention can obtain the original frequency or cycle at a high speed and excellent precision from data with a relatively small sampling count, and thus can be applied to various analysis programs. Such a software program can be provided as a program stored in a medium such as a floppy disk, hard disk, magnetic recording medium, CD, and ROM that can be read by a computer or microprocessor.

Furthermore, the measurement device and measurement method according to the invention are of course not limited in their application to devices that measure pulse waves. For example, the device and the method can be applied to measuring body movement pitches using an acceleration sensor, and can be used to obtain output values such as the frequency and cycle of other cyclically changing data at high precision using small sampling counts. Particularly since the measurement device and measurement method according to the invention need only a small sampling count, they are extremely suitable to measuring low-frequency data that requires long sampling time, and are suitable to measuring data related to the human body, such as number of breaths, in addition to pulse count and body movement pitch described above.

Note that the numbers such as the resolution referenced in the above explanation are merely examples, and that the invention is of course not limited to these numbers.

Overall Configuration of the Portable Electronic Instrument

The aforementioned portable electronic instrument equipped with the measurement function according to the invention will be explained in more details below.

Returning to FIGS. 1A and 1B, pulse wave detection sensor unit 30 is connected via cable 20 to main body 10 of portable electronic instrument 1 in this embodiment, having the wristwatch structure. Connector piece 80 is provided on the tip side of cable 20, and said connector piece 80 can be detachably installed in connector area 70 provided on the 6 o'clock side of device main body 10. Pulse wave detection sensor unit 30 is attached to the area between the base and the first joint of the index finger and is shielded from light by sensor-fastening strap 40. Attaching pulse wave detection sensor unit 30 to the base of a finger in this way keeps cable 20 short and prevents it from getting in the way during running. Furthermore, taking into consideration the temperature distribution between the palm and finger tip in cold weather, the temperature at the finger tip falls substantially, while the temperature at the base of the finger falls relatively little. Therefore, attaching pulse wave detection sensor unit 30 at the base of the finger enables pulse count, etc. to be accurately measured even during a run outside on a cold day.

FIG. 12 shows main body 10 of the portable electronic instrument of this embodiment, with the wristband and cable removed; FIG. 13 shows a view of portable electronic instrument, obtained from the 3 o'clock direction of the main body.

As shown in FIG. 12, device main body 10 of this embodiment is provided with plastic watch case 11 (body case), and the top side of this watch case 11 is provided with liquid crystal display device 13 (display device) with an EL backlight for displaying running time, pitch during walking, and pulse wave information such as pulse count, in addition to current time and date. Liquid crystal display device 13 is provided with first segment display area 131 positioned on the upper left side of the display surface, second segment display area 132 positioned on the upper right side of the display surface, third segment display area 133 positioned on the lower right side of the display surface, and dot display area 134 positioned on the lower left side of the display. Dot display area 134 can graphically display various types of information.

As explained above, control area 5, which performs various types of control and data processing in order to determine the change in pulse count based on the data detected by pulse wave detection sensor unit 30 and to display the result on liquid crystal display device 13, is provided inside watch case 11. Control area 5 is also provided with a timing circuit and thus can display normal time, lap time, split time, etc. on liquid crystal display device 13.

Button switches 111 through 115, which are used for external operations such as time adjustment and display mode switching, are provided on the perimeter of watch case 11. Additionally, larger button switches 116 and 117 are provided on the surface of the watch case. Furthermore, button-shaped small battery 59 which acts as the power supply for portable electronic instrument 1 is housed inside watch case 11, and electrical power can also be supplied from battery 59 to pulse wave detection sensor unit 30 via cable 20. This cable 20 is also used for inputting the detection result of pulse wave detection sensor unit 30 into control area 5 of watch case 11.

Because portable electronic instrument 1 of this embodiment is a multi-function device, the size of device main body 10 must be increased as more functions are added. However, it is difficult to extend device main body 10 in the 6 or 12 o'clock directions of the watch because it must be worn around a wrist. Therefore, in this embodiment, by using watch case 11 which is longer in the 3 and 9 o'clock directions than in the 6 and 12 o'clock directions, device main body 10 can house a control area that can implement a large number of functions or other functional units. Even though watch case 11 is extended in the 3 and 9 o'clock directions, wristband 12 is connected eccentrically toward the 3 o'clock side, leaving large extended area 101 in the 9 o'clock direction of the wristwatch, viewed from wristband 12. However, no such extended area is provided in the 3 o'clock direction. Consequently, this structure, despite the use of long watch case 11, allows free wrist movement and eliminates the possibility of the back of the hand striking watch case 11 during a fall.

Flat piezoelectric element 58 for a buzzer is positioned in the 9 o'clock direction, viewed from battery 59, inside watch case 11. Battery 59 which is heavier than piezoelectric element 58 is positioned eccentrically in the 3 o'clock direction so that the center of gravity of device main body 10 is shifted in the 3 o'clock direction. Because wristband 12 is connected to a spot near this center of gravity, device main body 10 can be securely attached to the wrist. Furthermore, the positioning of battery 59 and piezoelectric element 58 in the planar direction allows device main body 10 to be thin, and battery cover 118 installed on the back side as shown in FIG. 13 allows the user to easily replace battery 59.

As shown in FIG. 13, connecting area 105 for holding stopping pin 121 installed on the end of wristband 12 is formed in the 12 o'clock direction of watch case 11. Receiving area 106 is provided in the 6 o'clock direction of watch case 11, and fastener 122 for holding in place the middle point of wristband 12 wound around the wrist and folded back in the longitudinal direction of the band, is formed on said receiving area 106.

In the 6 o'clock direction of device main body 10, the area from bottom surface 119 to receiving area 106 is formed as an integral part of watch case 11 and forms rotation stop area 108 which is positioned at approximately 115° from bottom surface 119. That is, when wristband 12 is used to attach device main body 10 to top area L1 (side of the back of the hand) of right wrist L (arm), bottom surface 119 of watch case 11 tightly contacts top area L1 of wrist L while rotation stop area 108 contacts side area L2 where radius R is located. In this state, bottom surface 119 of device main body 10 more or less straddles radius R and ulna U, while rotation stop area 108 and the area between bent area 109 of bottom surface 119 and rotation stop area 108 contact radius R. Because rotation stop area 108 and bottom surface 119 form an anatomically ideal angle of approximately 115° as explained above, device main body 10 will not turn around arm L even if an attempt is made to turn it in the direction of arrow A or B. Furthermore, because the rotation of device main body 10 is restricted only in two locations on the side of the arm by bottom surface 119 and rotation stop area 108, bottom surface 119 and rotation stop area 108 securely contact the arm even if it is thin, and provide a secure rotation stopping effect and comfortable fit even if the arm is thick.

Configuration of the Pulse Wave Detection Sensor Unit

FIG. 14 shows a cross-section of the pulse wave detection sensor unit of this embodiment. In pulse wave detection sensor unit 30 of this embodiment, component housing space 300 is formed by placing back lid 302 on the bottom side of sensor frame 36 which constitutes a casing body. Circuit board 35 is positioned inside component housing space 300. LED 31, phototransistor 32, and other electronic components are mounted on circuit board 35. One end of cable 20 is fastened to pulse wave detection sensor unit 30 by bushing 393, and various wires of cable 20 are soldered to various patterns on circuit board 35. As shown in FIG. 1B, pulse wave detection sensor unit 30 is attached to the finger such that cable 20 is extended from the base of the finger toward device main body 10. Therefore, LED 31 and phototransistor 32 are arranged along the length of the finger, with LED 31 positioned on the finger tip side and phototransistor 32 positioned at the base of the finger. This configuration provides the effect of making it difficult for the ambient light to reach phototransistor 32.

In pulse wave detection sensor unit 30, a light transmission window is formed by translucent plate 34 which is made of a glass plate on the upper area of sensor frame 36, and the light-emitting surface and light-receiving surface of LED 31 and phototransistor 32, respectively, are oriented toward said translucent plate 34. Because of such a configuration, when a finger surface is pressed onto external surface 341 of translucent plate 34, LED 31 emits light toward the finger surface and phototransistor 32 can receive part of the light emitted by LED 31 that is reflected by the finger. Note that external surface 341 of translucent plate 34 protrudes farther than surrounding area 361 in order to improve its contact with the finger surface.

In this embodiment, an InGaN (indium-gallium-nitrogen) blue LED is used as LED 31, and its emission spectrum possesses a peak at 450 nm and its emission wavelength ranges from 350 to 600 nm. To match with LED 31 possessing such characteristics, a GaAsP (gallium-arsenic-phosphorus) phototransistor is used as phototransistor 32, and the light-receiving wavelength of the element itself ranges from 300 to 600 nm, with some sensitive areas also at or below 300 nm.

When pulse wave detection sensor unit 30 thus configured is attached to the base of the finger by sensor-fastening strap 40 and light is emitted from LED 31 toward the finger, the light reaches blood vessels, and part of the light is absorbed by the hemoglobin in the blood and part of it is reflected. The light reflected by the finger (blood) is received by phototransistor 32, and the change in the amount of received light corresponds to the change in the blood volume (pulse wave in the blood). That is, because the reflected light becomes weak when the blood volume is high and becomes strong when the blood volume is low, data such as pulse count can be measured by optically detecting the intensity of the reflected light as a pulse wave signal.

This embodiment uses LED 31 with an emission wavelength range of between 350 and 600 nm and phototransistor 32 with a light-receiving wavelength range of between 300 and 600 nm, and vital information is displayed based on the results taken in the overlapping wavelengths of between approximately 300 and approximately 600 nm, i.e., wavelengths of approximately 700 nm or shorter. When such pulse wave detection sensor unit 30 is used, even if the ambient light strikes the exposed part of the finger, lights with wavelengths of 700 nm or shorter contained in the ambient light do not use the finger as a light guide to reach phototransistor 32 (light-receiving area). The reason for this is as follows. Because lights with wavelengths of 700 nm or shorter contained in the ambient light do not easily penetrate the finger, the ambient light reaching the area of the finger not covered by the sensor fastening strap 40 will not penetrate the finger to reach phototransistor 32. In contrast, if an LED possessing an emission peak at around 880 nm and a silicon phototransistor are used, a light-receiving wavelength range of between 350 and 1,200 nm will result. In such a case, changes in the ambient light level tend to cause measurement errors because pulse waves will be detected using a light with 1 mm wavelength which can use the finger as a light guide to easily reach phototransistor 32.

Furthermore, because pulse wave information is obtained using lights with approximately 700 nm or shorter wavelengths, the S/N ratio of the pulse wave signal based on blood volume change is high. The reason for this is as follows. The absorption coefficient of hemoglobin in the blood for lights with wavelengths of between 300 and 700 nm is several times to approximately one hundred or more times larger than the absorption coefficient for a light with wavelength of 800 nm which has been conventionally used as the detection light. As a result, lights with wavelengths of between 300 and 700 nm change sensitively to blood volume changes, producing higher pulse wave detection rate (S/N ratio) based on blood volume change. By measuring such data having a high detection rate using the aforementioned measurement method, accurate pulse counts can be determined at high speeds.

As explained above, the measurement device and measurement method according to the present invention correct output values, such as pulse counts indicating the peak obtained through frequency analysis, using the side lobe values that appear on both sides of the peak, and thus can provide highly precise output values without increasing the number of sampling points. Consequently, the invention can provide highly precise output values without extending the data fetch time or tightening the specification of the measurement device. Therefore, the measurement device and measurement method according to the invention are ideal for portable, compact, multi-function electronic instruments which use digital measurement processes, and can be applied to a wide variety of measurements in the future.

Industrial Application Potential

The present invention relates to a measurement device and a measurement method that measure cyclically changing data, such as pulse wave, and produce output values such as pulse count. Because the invention can improve the precision of the output values without increasing the sampling count, it is ideal for portable, compact, multi-function electronic instruments equipped with functions such as pulse count measurement function.

We claim:

1. A measurement device comprising:

analysis means for analyzing a frequency of cyclically changing detection data obtained from a sensor and for producing an analysis result as digital data having a first resolution; and derivation means for deriving one of a cycle and a frequency as an output value based on the analysis result from said analysis means, wherein said derivation means corrects the output value indicating a peak value in the analysis result using a side lobe value that appears adjacent to and on at least one side of said peak, and derives the output value of the detection data at a second resolution that is higher than the first resolution.

2. A measurement device according to claim 1, wherein said derivation means comprises:

correction direction determination means for selecting one of a first and second side lobe values used for correction by said derivation means by comparing magnitudes of the first lobe value, the second lobe value, and the peak value; and correction magnitude calculation means for determining a correction magnitude by comparing the magnitude of the peak value with the magnitude of the selected one of the first and second side lobe values selected by said correction direction determination means and for correcting the output value indicating the peak value.

3. A measurement device according to claim 2, wherein said correction magnitude calculation means uses a digital value approximate a mesial magnitude of the first resolution as a maximum of the correction magnitude, and wherein said correction magnitude calculation means then calculates the correction magnitude using a predetermined function to convert a ratio of the magnitude of the selected one of the first and second lobes selected by said correction direction determination means.

4. A portable electronic instrument having a sensor that can detect cyclically changing data, said portable electronic instrument comprising:

a control device for processing signals from the sensor, said control device comprising an analyzer for analyzing a frequency of the cyclically changing data detected by said sensor and for producing an analysis result as digital data having a first resolution, and a deriving device for deriving one of a cycle and a frequency as an output value from the analysis result, wherein said deriving device corrects the output value indicating a peak value in the analysis result using a side lobe value that appears adjacent to and on at least one side of said peak, and wherein said deriving device derives the output value of the detection data having a second resolution that is higher than the first resolution; and a display device that can display the output from said control device.

5. A method for measuring of cyclically changing detection data comprising the steps of:

(a) analyzing a frequency of the cyclically changing detection data and producing an analysis result as digital data having a first resolution; and (b) deriving one of a cycle and frequency as an output value based on the analysis result from step (a) and correcting the output value indicating a peak value in the analysis result, using a side lobe value that appears adjacent to and on at least one side of said peak, and deriving the output value of the detection data at a second resolution that is higher than the first resolution.

6. A method according to claim 5, wherein step (b) further comprises the steps of:

(c) selecting one of a first and second side lobe values used for correction by comparing magnitudes of the first lobe value, the second lobe value, and the peak value; and (d) determining a correction magnitude by comparing the magnitude of the peak value with the magnitude of the selected one of the first and second side lobe values selected and for correcting the output value indicating the peak value.

7. A method according to claim 6, wherein step (c) further comprises the steps of:

using a digital value approximate a mesial magnitude of the first resolution as a maximum of the correction magnitude; and then calculating the correction magnitude using a predetermined function to convert a ratio of the magnitude of the selected one of the first and second lobes.

8. An apparatus for measuring cyclically changing detection data comprising:

frequency analyzer for performing a frequency analysis of the cyclically changing detection data to obtain frequency analysis data having a first resolution;

peak detector for detecting a peak value of the frequency analysis data obtained by said frequency analyzer;

correction direction determination means for determining whether a correction direction is one of (1) less than the peak value, and (2) at least the peak value; and correction magnitude calculation means for determining a correction magnitude by comparing the intensity of said peak with that of the correction direction in accordance with said correction direction determination means and then corrects said output value indicating said peak to obtain a corrected peak value having a second resolution greater than the first resolution.

9. An article of manufacture, comprising:

a computer readable medium having computer readable code storage means embodied therein for measuring cyclically changing detection data, the computer readable code storage means comprising:

computer readable program code for performing a frequency analysis of the cyclically changing detection data to obtain frequency analysis data having a first resolution:

computer readable program code for determining a peak of the frequency analysis data;

computer readable program code for determining whether a correction direction is one of (1) less than the peak, and (2) at least the peak; and computer readable program code for determining a correction magnitude by comparing the intensity of said peak with that of the correction direction and then corrects said output value indicating said peak to obtain a corrected peak value having a second resolution greater than the first resolution.

* * * * *

UNITED STATES PATENT AND TRADEMARK OFFICE
CERTIFICATE OF CORRECTION

PATENT NO. : 6,023,662
DATED : February 08, 2000
INVENTOR(S) : Motomu Hayakawa, et al.

It is certified that error appears in the above-identified patent and that said Letters Patent is hereby corrected as shown below:

Column 15:
Line 1, insert --side-- after "first" and again after "second".
Line 16, insert --side-- after "first" and again after "second".
Line 52, insert --side-- after "first" and again after "second".

Column 16:
Line 13, insert --side-- after "second".

Signed and Sealed this

Nineteenth Day of June, 2001

Attest:

*Attesting Officer*

NICHOLAS P. GODICI
*Acting Director of the United States Patent and Trademark Office*